United States Patent
Bonnefin et al.

(10) Patent No.: US 10,350,326 B2
(45) Date of Patent: Jul. 16, 2019

(54) WOUND DRESSING

(71) Applicant: CONVATEC TECHNOLOGIES INC., Las Vegas, NV (US)

(72) Inventors: Wayne Lee Bonnefin, Flintshire (GB); Ander Albizuri Bugedo, Flintshire (GB); David Parsons, Flintshire (GB); Joseph Thompson, Flintshire (GB)

(73) Assignee: Convatec Technologies Inc., Las Vegas, NV (US)

( * ) Notice: Subject to any disclaimer, the term of this patent is extended or adjusted under 35 U.S.C. 154(b) by 0 days.

(21) Appl. No.: 14/403,954

(22) PCT Filed: May 30, 2013

(86) PCT No.: PCT/GB2013/051443
§ 371 (c)(1),
(2) Date: Nov. 25, 2014

(87) PCT Pub. No.: WO2013/179047
PCT Pub. Date: Dec. 5, 2013

(65) Prior Publication Data
US 2015/0104486 A1  Apr. 16, 2015

(30) Foreign Application Priority Data
May 31, 2012 (GB) .................................. 1209745.7

(51) Int. Cl.
| | | |
|---|---|---|
| A61L 15/60 | (2006.01) | |
| A61L 15/28 | (2006.01) | |
| A61L 15/18 | (2006.01) | |
| A61F 13/00 | (2006.01) | |
| A61L 15/42 | (2006.01) | |
| A61L 15/46 | (2006.01) | |

(52) U.S. Cl.
CPC ........ *A61L 15/60* (2013.01); *A61F 13/00042* (2013.01); *A61F 13/00068* (2013.01); *A61L 15/18* (2013.01); *A61L 15/28* (2013.01); *A61L 15/42* (2013.01); *A61L 15/46* (2013.01); *A61L 2300/104* (2013.01)

(58) Field of Classification Search
None
See application file for complete search history.

(56) References Cited

U.S. PATENT DOCUMENTS

2004/0242108 A1* 12/2004 Russell .................. A01G 1/002
   442/414
2010/0030170 A1  2/2010 Keller et al.

FOREIGN PATENT DOCUMENTS

| AU | 2013269330 B2 | 7/2016 |
|---|---|---|
| CA | 2268344 A1 | 10/2000 |
| CA | 2268344 A1 | 10/2000 |
| GB | 2377177 A | 1/2003 |
| GB | 2377177 A | 1/2003 |
| GB | 2464970 A | 5/2010 |
| JP | 2004512063 A | 4/2004 |
| JP | 2004514505 A | 5/2004 |
| JP | 2008544794 A | 12/2008 |
| JP | 2011515136 A | 5/2011 |
| JP | 2011521675 A | 7/2011 |
| WO | WO 93/12275 | 6/1993 |
| WO | WO 94/16746 | 8/1994 |
| WO | WO 00/01425 | 1/2000 |
| WO | WO-0213750 A2 | 2/2002 |
| WO | WO 02/43743 A | 6/2002 |
| WO | WO-0243743 A1 | 6/2002 |
| WO | WO-2004084961 A1 | 10/2004 |
| WO | WO-2007003905 A1 | 1/2007 |
| WO | WO-2009115804 A2 | 9/2009 |
| WO | WO 2009/136160 A1 | 11/2009 |
| WO | WO-2009136160 A1 | 11/2009 |
| WO | WO 2013/179047 A1 | 12/2013 |

OTHER PUBLICATIONS

PCT/GB2013/051443 International Preliminary Report on Patentability dated Dec. 2, 2014.
PCT/GB2013/051443 Written Opinion completed Jul. 25, 2013.
PCT/GB2013/051443 International Search Report completed Jul. 25, 2013.
Chinese Patent Application No. 201380028751.8 Second Office Action dated Nov. 8, 2016.
Egyptian Patent Application No. PCT 1925/2014 Office Action dated Sep. 26, 2016 (with foreign associate reporting letter in English).
New Zealand Patent Application No. 702489 First Examination Report dated Sep. 15, 2016.
European Patent Application No. 13726839.7 Communication dated Nov. 8, 2016.
Mexican Patent Application No. MX/a/2014/014377 Office Action dated Apr. 2, 2017.
Russian Patent Application No. 2014153900 Office Action dated Mar. 13, 2017.
United Kingdom Patent Application No. 1421899.4 Examination Report dated Mar. 27, 2017.
European Patent Application No. 13726839.7 Communication dated Nov. 14, 2017.
Russian Patent Application No. 2014153900 Office Action dated Jan. 10, 2018.
Chile Patent Application No. 3240-2014 Office Action dated Oct. 25, 2017.
Great Britain Patent Application No. 1421899.4 Examination Report dated Nov. 1, 2017.
Malaysia Patent Application No. PI 2014003333 Substantive Examination Adverse Report dated Oct. 31, 2017.
Mexican Patent Application No. MX/a/2014/014377 Office Action dated Sep. 7, 2017.
Great Britain Patent Application No. 1421899.4 Examination Report dated Jun. 11, 2018.
Israeli Application No. 235857 Office Action dated May 2, 2018.
United Arab Emirates Patent Application No. 1308/204 Examination and Search Report dated Apr. 29, 2018.
Chinese Patent Application No. 201380028751.8 Office Action dated Apr. 1, 2016.
Japan Patent Application No. 2015-514591 Office Action dated Feb. 27, 2018.
United Kingdom Patent Application No. 1421899.4 Examination Report dated Mar. 28, 2018.
Dominican Republic Patent Application No. P2014-0275 Memo dated May 20, 2017.
Japanese Patent Application No. 2015-514591 Office Action dated Jun. 29, 2017.
New Zealand Patent Application No. 702489 Further Examination Report dated Jun. 30, 2017.

* cited by examiner

*Primary Examiner* — Jeffrey T. Palenik
(74) *Attorney, Agent, or Firm* — Wilson Sonsini Goodrich & Rosati

(57) ABSTRACT

A wound dressing comprising a mat of gel forming fibers comprising silver, the mat having an open structure reinforced with textile fibers or threads, or fibers or threads of limited absorbency for use in the treatment of wounds.

15 Claims, 1 Drawing Sheet

% Weight loss over time

| Time (Hrs) | 0 | 1 | 2 | 3 | 4 | 5 | 7 | 24 | 25 | 26 | 27 | 28 | 29 | 30 | 31 | 32 | 48 |
|---|---|---|---|---|---|---|---|---|---|---|---|---|---|---|---|---|---|
| HF-2010/200 | 0.00 | 9.87 | 13.73 | 17.57 | 22.29 | 25.57 | 32.21 | 61.94 | 63.90 | 65.67 | 67.26 | 69.04 | 70.79 | 72.72 | 74.96 | 76.78 | 93.85 |
| HF-2010/209 | 0.00 | 4.18 | 6.43 | 8.76 | 11.43 | 13.44 | 16.99 | 36.07 | 37.23 | 38.32 | 39.39 | 40.54 | 41.78 | 43.07 | 44.52 | 45.75 | 60.00 |
| HF-2010/211 | 0.00 | 3.75 | 5.82 | 8.33 | 11.22 | 13.44 | 17.98 | 41.55 | 42.90 | 44.08 | 45.23 | 46.43 | 47.59 | 48.85 | 50.16 | 51.19 | 64.31 |
| HF-2010/214 | 0.00 | 3.53 | 5.79 | 8.14 | 11.05 | 13.18 | 17.41 | 38.69 | 40.09 | 41.24 | 42.38 | 43.60 | 45.01 | 46.39 | 48.07 | 49.34 | 65.15 |
| HF-2010/218 | 0.00 | 5.76 | 9.91 | 14.05 | 18.59 | 22.46 | 29.39 | 65.11 | 66.75 | 68.22 | 69.73 | 71.22 | 73.03 | 74.65 | 76.29 | 77.66 | 90.02 |
| HF-2010/219 | 0.00 | 5.17 | 8.60 | 12.01 | 15.74 | 19.01 | 25.27 | 57.27 | 58.95 | 60.46 | 61.98 | 63.51 | 65.24 | 66.85 | 68.54 | 70.10 | 87.05 |
| HF-2010/223 | 0.00 | 3.20 | 5.57 | 7.81 | 10.42 | 12.70 | 16.79 | 37.56 | 38.76 | 39.86 | 40.92 | 41.99 | 43.22 | 44.41 | 45.68 | 46.79 | 59.10 |
| HF-2010/225 | 0.00 | 3.74 | 6.44 | 9.01 | 11.92 | 14.51 | 18.75 | 42.38 | 43.69 | 44.84 | 46.35 | 47.89 | 49.55 | 51.18 | 53.01 | 54.54 | 71.20 |
| HF-2010/226 | 0.00 | 3.13 | 5.94 | 8.54 | 11.66 | 14.52 | 19.46 | 47.47 | 48.95 | 50.33 | 51.85 | 53.35 | 55.00 | 56.63 | 58.32 | 59.67 | 74.91 |
| HF-2010/216A | 0.00 | 3.21 | 6.53 | 9.54 | 13.19 | 16.10 | 20.86 | 43.02 | 44.15 | 45.21 | 46.36 | 47.50 | 48.86 | 50.17 | 51.61 | 52.81 | 67.82 |
| HF-2010/216B | 0.00 | 2.96 | 6.59 | 9.51 | 12.98 | 16.08 | 20.78 | 40.85 | 42.03 | 43.23 | 44.57 | 45.93 | 47.47 | 49.09 | 50.81 | 52.28 | 68.44 |

WOUND DRESSING

CROSS-REFERENCE

This application is a U.S. National Phase of PCT/GB2013/051443, filed May 30, 2013, which claims the benefit of priority of GB 1209745.5, filed May 31, 2012, each of which is incorporated herein by reference in their entirety.

The present invention relates to wound dressings having antibacterial, antiviral and/or antifungal activity, to a method of producing such dressings and the use of such dressings in the treatment of wounds. In particular, the invention relates to the dressings for use in the treatment of infected or dehydrated wounds or wounds with scant exudate.

With the rise in antimicrobial resistance and a general call to reduce the use of antibiotics, silver is gaining increasing popularity as an effective antimicrobial agent. The advantage of using silver as an antimicrobial agent is that there is no formation of bacterial tolerance. This is in contrast for instance to many antibiotics. A major drawback when using ionic or metallic silver for antimicrobial purposes is however the lack of control over release of the silver ions within and from the delivery vehicle.

In the past it has been known to deliver silver ions by the use of a simple solution of silver nitrate. It is also known to deliver silver by the use of a complex with sulfadiazine. Silver sulfadiazine is used extensively in the treatment of wounds, and particularly burns, and is incorporated in a cream base and sold under the trademark Flamazine or Silvadene. As the silver is present in such products as a complex, its solubility in wound fluid is low and hence the quantity of active silver present is also low.

It is also known to deliver silver ions from a wound dressing such as those comprising a gelling fibre as found in AQUACEL® Ag. These dressings comprise gel forming fibres which have been ion exchanged with for instance silver nitrate to incorporate silver ions into the fibres. When in contact with an exuding wound, the dressing takes up moisture and releases the silver to the exudate and the wound itself. As it is the presence of moisture (exudate) in the dressing that enables the silver ions to be released, it would be expected that the state of hydration of the dressing would affect the duration for which silver is available and the quantity of silver that is available. It could be expected that on application of the dressing to the wound, the release of silver ions from the dressing would be initially high but tail off over time as the dressing dehydrates. This could happen for instance if the amount of exudate produced by the wound is insufficient to maintain hydration in the dressing, or if the rate of evaporation of moisture from the dressing is high or at least exceeds the rate of absorption from the wound.

It is generally recognised that healing is assisted by the maintenance of a moist wound healing environment. A dry dressing therefore not only limits the supply of silver ions to the wound from a silver containing dressing, it also deprives the wound of the benefits of moist wound healing. In addition, a dry dressing may adhere to the wound causing tissue damage on removal.

There thus exists a need for a dressing which sustains the release of silver ions to the wound by reducing the tendency for the dressing to dehydrate during its wear time.

There is also a need for a dressing with a reduced tendency to adhere to the wound either by reducing the tendency for the dressing to dehydrate during its wear time or by a slow rate of hydration from the wound.

There is also a need for a wound dressing with a sustained release of silver ions which maintains an effective concentration of silver ions in the wound over its wear time assisted by providing a sustained hydration in the dressing over that wear time.

A sustained release of silver ions into the wound is assisted by a dressing which does not readily dehydrate and thus maintains moisture in the dressing for a longer time.

We have now found that wound dressings can be prepared which give a controlled, sustained release of silver ions within the dressing and into the adjacent wound fluid to give antimicrobial activity and moist wound healing over the wear time. Surprisingly, the required hydration property is provided by a dressing comprising an open structure of woven or nonwoven gel forming fibres. By open structure is meant a regular or irregular, two or three dimensional construct with a large volume for a given mass in which the free internal fabric volume exceeds the solid fibre volume.

It is thought that the open structure allows moisture to be retained between the fibres as well as in the fibres themselves and that this contributes to the maintenance of moisture in the dressing.

In the past, open structures were not thought to be practical for use on wounds because the open structure on its own lacks the integrity when gelled to be removed from the wound in one piece. Collapse or fragmentation of the dressing necessitates flushing of the wound with the risk of possible retention of parts of the used dressing in the wound. However, the integrity of open structures can be improved with reinforcement from other fibres or threads such as textile fibres or threads or fibres with less ability to absorb and gel.

Accordingly, the invention provides for a wound dressing comprising a mat of gel forming fibres comprising silver, the mat having an open structure reinforced with textile fibres or fibres or threads of limited absorbency for use in the treatment of infected wounds.

Such dressings may have the advantage that hydration is maintained over the wear time of the dressing so that a prolonged delivery of silver ions is experienced by the wound. This is thought to be due to the combination of the open structure of the fibrous mat and the non-gel forming fibres providing the necessary integrity to allow the dressing to be removed from the wound in one piece at the end of its wear time.

Preferably the open structure of the fibrous mat is provided by a nonwoven fibrous mat that has been entangled by fluid jet entanglement such as hydro entanglement or needle punching. The open structure may be defined by the extent of entanglement in the dressing. The extent of entanglement may be expressed as the number of entanglements per square centimetre or more usually by a punch density. Preferably the nonwoven fibrous mat is needle punched or entangled to a punch density of less than 60 per $cm^2$, and more preferably from 50 to 10 per $cm^2$. Most preferably the punch density is from 40 to 10 per $cm^2$ In fluid entanglement the jet pressure, diameter and spacing also give a density of entanglement equivalent to a needle punch density in that they give a number of entanglements per square centimetre.

The fibrous mat of gel forming fibres preferably has a basis weight of from 30 to 1000 grams per square meter. More preferably the basis weight is from 100 to 200 grams per square meter and most preferably from 150 to 200 grams per square meter.

Preferably the dressing has a rate of moisture loss at least 25% lower than a dressing made from a mat with a needle punch density of 60 per cm² or higher. More preferably the rate of moisture loss is from 30% to 6% lower than that from a dressing with a needle punch density of 60 per cm² or higher.

Preferably the dressing maintains the hydration of the wound by having a rate of moisture loss (as measured by the percentage weight loss from the dressing) of less than 75% over the first 48 hours of wear. More preferably the rate of moisture loss is from 70% to 5% over the first 48 hours of wear.

Preferably the nonwoven fibrous mat is reinforced with textile fibres blended with the gel-forming fibres during the formation of the mat. Alternatively, the textile fibres are present as a thread or yarn stitch-bonded on the fibrous mat for instance as described in PCT/GB2009/001138.

We have found that a desired final concentration of silver in the dry wound dressing is between about 0.1% and 2% by weight, for example. Preferably between 0.1% to 10% by weight and more preferably between 0.5% and 5% by weight of the dressing. Such concentrations can be achieved by the preparation method described in WO02/43743A.

We have also found that a desired concentration of ionic silver released by the dressing into water is preferably less than 1.5 ppm and, more preferably, between 1.5 ppm and 0.5 ppm. Most preferably the concentration of ionic silver released by the dressing into water is about 1 ppm.

By gel forming fibres is meant hygroscopic fibres which upon the uptake of wound exudate become moist slippery or gelatinous and thus reduce the tendency for the surrounding fibres to adhere to the wound. The gel forming fibres can be of the type which retain their structural integrity on absorption of exudate or can be of the type which lose their fibrous form and become a structureless gel. The gel forming fibres are preferably spun sodium carboxymethylcellulose fibres, chemically modified cellulosic fibres, cellulose ethyl sulphonate fibres, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit or equivalent ethyl sulphonate. The gel forming fibres preferably have an absorbency of at least 5 grams 0.9% saline solution per gram of fibre (as measured by the free swell absorbency method BS EN 13726-1:2002 Test methods for primary wound dressings—Part 1: Aspects of absorbency, Method 3.2 free swell absorptive capacity).

Preferably the gel forming fibres have an absorbency of at least 10 g/g as measured in the free swell absorbency method, more preferably between 15 g/g and 30 g/g.

Preferably the textile fibres have an absorbency of less than 10 g/g as measured by the free swell method and more preferably less than 5 g/g. The dressing may for instance comprise non gel forming fibres and in particular textile fibres such as Lyocell (sometimes branded as Tencel®), cotton or viscose and may comprise elastane (sometimes branded as Spandex or Lycra®) or other elastic fibre.

The wound dressing may comprise a fibrous mat in the form of a strip or a roll with an open structure and comprising gel forming fibres, the strip having longitudinal lines of stitches formed from a thread and optionally transverse lines of stitches formed from a thread. The longitudinal stitching is longitudinal in that it is generally parallel to the long dimension of the strip.

The transverse stitching is transverse in that it joins the longitudinal lines of stitches together and in some embodiments is generally perpendicular to the long dimension of the strip.

The thread may be a single filament or multiple filament yarn or a staple fibre yarn. The thread can be cellulosic, elastane, nylon, polyester or polyurethane. The thread can be impregnated with an active agent for example with an antimicrobial agent or confer other properties such as radio-opaque qualities.

The dressing may be stitched with lines of longitudinal stitching from 1 mm to 10 mm apart and preferably from 2 mm to 5 mm apart. The lines of longitudinal stitching may be a lock stitch and may typically be crochet or chain stitch but other stitch patterns may also be used. The dressing may also comprise rows of transverse stitches; the rows of transverse stitching may be from 1 to 10 mm apart and preferably from 2 to 5 mm apart. The transverse lines of stitches may be a pattern stitch and may be crocheted or may be a basting stitch between two layers of superposed gel forming fibres. Preferably, the lines of stitching are made in a thread such as lyocell. The transverse stitches serve to link adjacent longitudinal lines of stitches together to add strength to the dressing in a transverse direction.

Modification of cellulose fibres can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation or ethyl sulphonation required and will be readily apparent to the person skilled in the art. They may be identical or similar to those described in WO 93/12275, WO 94/16746 or WO 00/01425 to which the reader is directed for further detail.

Desirably the chemical modification is carried out in the presence of industrial methylated spirits (IMS), and IMS is preferably also used in a subsequent washing step, suitably along with water, as a cleaner and steriliser. The degree of substitution is desirably such that upon absorption of exudate the fibres at the skin-contacting surface of the dressing form a gel.

The open structure of the fibrous mat may be provided by a nonwoven mat of gel-forming fibres made by a needle felting/carding technique to form a web. The mat may have an antimicrobial material incorporated into it and in particular silver by the method described in WO 02/43743. The roll may be stitched in the longitudinal direction with lines of stitching in lyocell yarn. The longitudinal lines of stitches may be supplemented by transverse lines of stitching in the form of continuous, angular zigzags which extend between adjacent longitudinal lines of stitches. In this way stitch free gaps are left between columns of longitudinal stitching. The roll may be slit in the longitudinal direction in the stitch free gaps to form dressings of various sizes. For instance strips of 1 cm×45 cm, squares of 5 cm×5 cm or rectangles of 20 cm×30 cm.

The invention is illustrated by the following figures in which:

FIG. 1 is a table showing results from Example 1 below.

The invention is illustrated by the following examples.

EXAMPLE 1

The dehydration properties of various fibrous mats for use in wound dressings according to the invention were compared.

The fibrous mat samples used are detailed below in Table 1:

| Prototype | Description | |
|---|---|---|
| | Basis weight (g per m² or gsm) Dehydration Test | Needle Punch Density (punches per cm²) |
| HF-2010/200 | 88 | 60 |
| HF-2010/209 | 171 | 30 |
| HF-2010/211 | 181 | 30 |
| HF-2010/214 | 218 | 30 |
| HF-2010/216 | 104 | 15 |
| HF-2010/218 | 163 | 75 |
| HF-2010/219 | 163 | 100 |
| HF-2010/223 | 183 | 30 |
| HF-2010/225 | 184 | 50 |
| HF-2010/226 | 183 | 100 |

In the test, 5 cm×5 cm samples of the prototypes were immersed in an isotonic solution until fully hydrated and then placed on a petri dish. The dehydration rates of the prototypes were assessed gravimetrically as shown in FIG. 1.

FIG. 1 shows how the different degrees of needle punch density affected the hydration performance of the mats. Among the prototype mats that managed to retain the fluid for longer are:
HF-2010/223, HF-2010/29, HF-2010/211, HF-2010/214 and HF-2010/216.

Despite the basis weight differences of the prototypes tested, the best performing prototypes have all been textiled with a low needle punch density, for instance less than 60.

Table 2 shows the needle punch density against the % weight loss on drying for the samples in Table 1.

| | | | 24 hrs | | 48 hrs | |
|---|---|---|---|---|---|---|
| gsm | p/cm² | batch | % loss | Rank | % loss | Rank |
| 171 | 30 | HF-2010/209 | 36 | 1 | 60 | 2 |
| 183 | 30 | HF-2010/223 | 38 | 2 | 59 | 1 |
| 218 | 30 | HF-2010/214 | 39 | 3 | 65 | 4 |
| 104 | 15 | HF-2010/216 | 41 | 4 | 68 | 6 |
| 181 | 30 | HF-2010/211 | 42 | 5 | 64 | 3 |
| 184 | 50 | HF-2010/225 | 42 | 6 | 71 | 7 |
| 104 | 15 | HF-2010/216 | 43 | 7 | 68 | 5 |
| 183 | 100 | HF-2010/226 | 47 | 8 | 75 | 8 |
| 163 | 100 | HF-2010/219 | 57 | 9 | 87 | 9 |
| 88 | 60 | HF-2010/200 | 62 | 10 | 94 | 11 |
| 163 | 75 | HF-2010/218 | 65 | 11 | 90 | 10 |

The mats to be used in dressings according to the invention demonstrated that they can maintain a moist wound environment for a sustained period of time. It can be concluded, that a low needle punch density, provides a "loftier" structure which allows more space between the fibres to expand and gel, thus, increasing the absorption capacity. This structure also contributes to retaining the fluid for a longer time, therefore, drying out at a slower rate.

These results show that a dressing according to the invention maintains a moist wound environment for the wear time of a dressing.

EXAMPLE 2

A wound dressing according to the invention was made by preparing two mats of gel-forming fibres (carboxymethylcellulose) by carding, cross-lapping and needle punching to a needle punch density of 22 to make a mat of 70 gsm. The mats were impregnated with silver ions by the method described in WO/02 43743A to give a total silver content of around 1.18% based on the anhydrous dressing. The mats were placed one on top of the other and stitch-bonded by the method described in PCT/GB2009/001138 so that the weft stitches were in between the mats.

The release of silver from such a wound dressing was measured by silver assay using atomic absorption spectrophotometer (AAS) equipped with a silver hollow cathode lamp. In that method a dialysis membrane was pre-soaked in water for a minimum of 16 hours. Samples of the dressing are cut into 5 cm×5 cm squares and weighed. Each sample is placed into a pouch created from the prehydrated dialysis membrane and placed into 200 ml of isotonic saline at 37° C. contained within a suitable screw topped glass vessel and stirred by magnetic stirrer. A 10.0 ml aliquot from each vessel was taken at the following time-points: 3 h, 6 h, 24 h, 48 h, 72 h and 96 h and replaced with 10.0 ml of fresh saline in order to maintain the dissolution volume of 200 ml. The liquid samples were then assayed by AAS comparing to standard silver solutions of known concentration.

The results were as follows:

| Time point (hours) | Silver Released ppm (µg/ml) | Std Dev |
|---|---|---|
| 3 | 0.36 | 0.01 |
| 6 | 0.37 | 0.02 |
| 24 | 0.37 | 0.00 |
| 48 | 0.37 | 0.01 |
| 72 | 0.40 | 0.01 |
| 96 | 0.41 | 0.01 |

These results show that dressings according to the invention give a steady release of silver from the dressing.

EXAMPLE 3

This example shows the relationship between the hydration state of the optimized open structure fibrous mat and antimicrobial effectiveness.

An optimized open structure fibrous mat according to the invention consists of two gel forming 77 gsm mats stitch-bonded together following the method described in PCT/GB2009/001138. Each mat being comprised of carded, cross-lapped and needled punched sodium carboxymethylcellulose fibres (at a needle punch density of 22 per cm²) which have been previously impregnated with silver ions as described in WO02/43743A.

140 mm diameter pre-dried Tryptone Soy Agar (TSA) test plates were surface-inoculated with *Staphylococcus aureus* (NCIMB 9518) to create a confluent lawn and incubated for 4 hours at 35° C. to initiate growth. The surface of each plate was then totally covered with sterile prehydrated dialysis membrane. Dry 35 mm diameter optimized open structure fibrous mats, were placed on top of the dialysis membrane at the centre of each plate. In half the tests (n=3) the optimized open structure fibrous mat was saturated with isotonic saline (2 ml), for the other half of the tests the mat was left dry. Plates were incubated at 35° C. for 48 hours. The open structure fibrous mats were then removed and the plates re-incubated for a further 24 hours.

Results were as follows:—

| Condition | Visual Observation of Agar Plate |
| --- | --- |
| Dry | Growth beneath dressing (n = 3) |
| Hydrated | No Growth beneath dressing (n = 3) |

These results confirm that hydration is required for an antimicrobial effect to be exerted by the optimized open structure fibrous mat described. It is therefore possible to conclude that maintaining hydration for a longer period of time will extend the effective period of antimicrobial protection and will improve the overall antimicrobial effect.

EXAMPLE 4

This example shows the relationship between the rate of dehydration of optimized open structure fibrous mats and the ease of their removal from a fragile surface.

Fibrous mat 5 cm×5 cm samples of conventional 100 gsm fibre mats with a needle punch density of 60 per $cm^2$ and optimized open structure mats according to the invention as described in example 3 were fully hydrated by immersion in isotonic saline. Drained samples were placed on agar plates (tryptone 15 g/l, soy peptone 5 g/l, sodium chloride 5 g/l & Agar No. 2 12 g/l). Mats were then left to dehydrate in a forced-air cabinet for 24 hours at ambient room temperature (~22° C.). At this point, sample mats had become adhered to the agar surface and could not be removed without disrupting the agar. 10 ml of isotonic saline was then applied to each fibrous mat to start a rehydration process. Taking hold of the edge of the mat with tweezers, a constant gentle lifting force was applied. The time between application of the rehydrating solution and the successful non-disruptive removal of the mat from the agar surface was recorded.

The following results were obtained (results are expressed in seconds):—

| Sample replicate | Conventional fibre mat | Open structure mat according to the invention |
| --- | --- | --- |
| 1 | 290 | 40 |
| 2 | 255 | 60 |
| 3 | 347 | 23 |
| 4 | 241 | 48 |
| 5 | 331 | 49 |
| 6 | 280 | 40 |
| 7 | (no result - test error) | 50 |
| 8 | 274 | 36 |
| Average | 288 | 43 |

The conventional fibre mats had a drier appearance after 24 hrs on the agar surface and rehydration was visibly slower when compared to the optimized open structured mats. In clinical practice, dressings are likely to be changed at fixed intervals rather than when absorption capacity is reached or the dressing begins to adhere due to a reduction in the rate of exudation. There may also be limited time available to make dressing changes. Waiting for rehydration may not therefore be an option. Given these circumstances, the invention offers a distinct advantage in that tissue damage caused by dressing change is less likely to occur with the optimized open structure mat according to the invention.

The invention claimed is:

1. A wound dressing comprising a mat of gel forming fibres comprising between about 0.1% and 20% by weight of silver, the mat having an open structure in which the free internal volume of the mat exceeds the solid fibres volume, and reinforced with fibres or thread of limited absorbency of less than 10 g/g as measured by the free swell method for use in the treatment of wounds, wherein the gel forming fibres and the fibres or thread of limited absorbency are blended during the formation of the mat, wherein the mat has a punch density of from 10 to 50 per $cm^2$, and wherein the basis weight of the mat is from 50 to 200 grams per square meter.

2. A wound dressing as claimed in claim 1 wherein the mat is further reinforced with stitch-bonding in a thread of textile fibre.

3. A wound dressing as claimed in claim 1 wherein the mat is further reinforced with stitch-bonding in a line of longitudinal stitches.

4. A wound dressing as claimed in claim 1 wherein the gel forming fibres are modified cellulose gel forming fibres.

5. A wound dressing as claimed in claim 1 wherein the dressing has a rate of moisture loss at least 25% lower than a dressing made from a mat with a punch density of 60 per $cm^2$ or higher.

6. A wound dressing as claimed in claim 1 wherein the dressing maintains the hydration of the wound by having a rate of moisture loss (as measured by the percentage weight loss from the dressing) of less than 75% over the first 48 hours of wear.

7. The wound dressing of claim 1, wherein the punch density is from 10 to 40 per $cm^2$.

8. A wound dressing comprising two superposed mats of gel forming fibres comprising between about 0.1% and 20% by weight of silver, each mat having an open structure in which the free internal volume of the mat exceeds the solid fibres volume, and reinforced with fibres or threads of limited absorbency of less than 10 g/g as measured by the free swell method for use in the treatment of wounds, wherein each mat has a punch density of from 10 to 50 per $cm^2$, and wherein the basis weight of the mat is from 50 to 200 grams per square meter.

9. A wound dressing as claimed in claim 8 wherein each mat is reinforced with textile fibres blended with the gel-forming fibres in each mat.

10. A wound dressing as claimed in claim 8 wherein the superposed mats are stich-bonded together with a thread of textile fibre.

11. A wound dressing as claimed in claim 8 wherein the superposed mats are stitch-bonded together with a line of longitudinal stitches.

12. A wound dressing as claimed in claim 8 wherein the gel forming fibres are modified cellulose gel forming fibres.

13. The wound dressing of claim 8, wherein the punch density is from 10 to 40 per $cm^2$.

14. A mat for treatment of wounds, said mat comprising gel forming fibres, and
between about 0.12% and 20% by weight of silver,
wherein said mat has an open structure in which the free internal volume of the mat exceeds the solid fibres volume, is reinforced with fibres or thread of limited absorbency of less than 10 g/g as measured by the free swell method, and has a punch density of from 10 to 50 per $cm^2$,
wherein the gel forming fibres and the fibres or thread of limited absorbency are blended during the formation of the mat, and wherein the basis weight of the mat is from 50 to 200 grams per square meter.

15. The mat of claim 14, wherein the punch density is from 10 to 40 per $cm^2$.

* * * * *